United States Patent
Reytier et al.

(10) Patent No.: US 9,963,791 B2
(45) Date of Patent: May 8, 2018

(54) METHODS FOR PRODUCING COMBUSTIBLE GAS FROM THE ELECTROLYSIS OF WATER (HTE) OR CO-ELECTROLYSIS WITH $H_2O/CO_2$ IN THE SAME CHAMBER, AND ASSOCIATED CATALYTIC REACTOR AND SYSTEM

(71) Applicant: COMMISSARIAT A L'ENERGIE ATOMIQUE ET AUX ENERGIES ALTERNATIVES, Paris (FR)

(72) Inventors: Magali Reytier, Villard de Lans (FR); Guilhem Roux, Saint-Egreve (FR)

(73) Assignee: COMMISSARIAT À L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 145 days.

(21) Appl. No.: 14/783,350

(22) PCT Filed: Apr. 7, 2014

(86) PCT No.: PCT/IB2014/060481
§ 371 (c)(1),
(2) Date: Oct. 8, 2015

(87) PCT Pub. No.: WO2014/167477
PCT Pub. Date: Oct. 16, 2014

(65) Prior Publication Data
US 2016/0053388 A1  Feb. 25, 2016

(30) Foreign Application Priority Data
Apr. 8, 2013 (FR) ..................... 13 53104

(51) Int. Cl.
*C25B 1/00* (2006.01)
*C25B 9/00* (2006.01)
(Continued)

(52) U.S. Cl.
CPC ............... *C25B 1/10* (2013.01); *C07C 1/041* (2013.01); *C07C 1/044* (2013.01); *C07C 1/0435* (2013.01);
(Continued)

(58) Field of Classification Search
CPC .... C25B 1/00; C25B 9/00; C25B 9/08; C25B 11/035; C25B 9/18; C25D 17/002; C25D 17/02
(Continued)

(56) References Cited

U.S. PATENT DOCUMENTS 3,976,556 A * 8/1976 De Nora ................ C25B 1/46
  204/262
6,183,703 B1 2/2001 Hsu et al.
(Continued)

FOREIGN PATENT DOCUMENTS

FR  2931168 A1  11/2009
FR  2999612 A1  6/2014

OTHER PUBLICATIONS

Ocampo, F. et al., "Methanation of carbon dioxide over nickel-based Ce0.72Zr0.28O2 mixed oxide catalysts prepared by sol-gel method," Applied Catalysis A: General, 2009, pp. 90-96, vol. 369.
(Continued)

Primary Examiner — Zulmariam Mendez
(74) Attorney, Agent, or Firm — Oliff PLC

(57) ABSTRACT

The invention relates to a novel reactor design, wherein the pressurized chamber contains both a high-temperature electrolysis (HTE) reactor with elementary electrolysis cell stacking for producing either hydrogen or a synthesis gas ("syngas" for a $H_2+CO$ mixture) from water vapor $H_2O$ and carbon dioxide $CO_2$, and at least one catalyst arranged at a distance and downstream of the outlet of the electrolyzer for converting the previously produced synthesis gas into the
(Continued)

Figure 1:
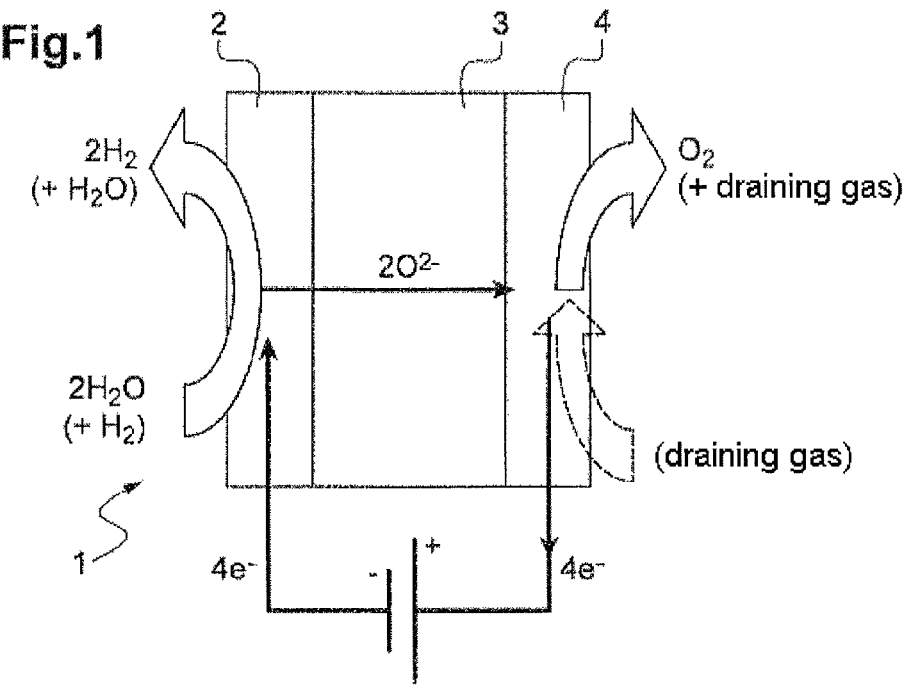

desired combustible gas, by means of heterogeneous catalysis, the synthesis gas having being produced either directly from the electrolysis reactor or indirectly by mixing the hydrogen produced with carbon dioxide $CO_2$ injected into the chamber.

34 Claims, 3 Drawing Sheets

(51) Int. Cl.
| | |
|---|---|
| C25B 9/08 | (2006.01) |
| C25D 17/02 | (2006.01) |
| C25B 9/18 | (2006.01) |
| C25B 1/10 | (2006.01) |
| C25B 15/08 | (2006.01) |
| C25B 1/12 | (2006.01) |
| C25B 3/04 | (2006.01) |
| H01M 8/0612 | (2016.01) |
| C07C 1/04 | (2006.01) |
| C07C 29/151 | (2006.01) |
| C07C 29/152 | (2006.01) |
| C07C 29/156 | (2006.01) |
| C07C 41/01 | (2006.01) |
| C10G 2/00 | (2006.01) |

(52) U.S. Cl.
CPC .......... *C07C 1/0485* (2013.01); *C07C 29/152* (2013.01); *C07C 29/156* (2013.01); *C07C 29/1518* (2013.01); *C07C 41/01* (2013.01); *C10G 2/332* (2013.01); *C10G 2/34* (2013.01); *C10G 2/50* (2013.01); *C25B 1/12* (2013.01); *C25B 3/04* (2013.01); *C25B 9/08* (2013.01); *C25B 9/18* (2013.01); *C25B 15/08* (2013.01); *H01M 8/0631* (2013.01); *Y02E 60/366* (2013.01); *Y02P 20/132* (2015.11)

(58) Field of Classification Search
USPC .......................................................... 204/242
See application file for complete search history.

(56) References Cited

U.S. PATENT DOCUMENTS

| | | |
|---|---|---|
| 2007/0163889 A1 | 7/2007 | Kato et al. |
| 2009/0289227 A1 | 11/2009 | Rising |
| 2012/0077099 A1 | 3/2012 | Crumm et al. |
| 2012/0171596 A1 | 7/2012 | Hilliard |
| 2012/0325654 A1 | 12/2012 | Le Gallo et al. |
| 2015/0329979 A1 | 11/2015 | Reytier et al. |

OTHER PUBLICATIONS

Tian, D. et al., "Bimetallic Ni-Fe total-methanation catalyst for the production of substitute natural gas under high pressure," Fuel, 2013, pp. 224-229, vol. 104.

Jul. 30, 2014 International Search Report issued in International Patent Application No. PCT/IB2014/060481.

Oct. 13, 2015 International Preliminary Report on Patentability issued in International Patent Application No. PCT/IB2014/060481.

* cited by examiner

METHODS FOR PRODUCING COMBUSTIBLE GAS FROM THE ELECTROLYSIS OF WATER (HTE) OR CO-ELECTROLYSIS WITH H₂O/CO₂ IN THE SAME CHAMBER, AND ASSOCIATED CATALYTIC REACTOR AND SYSTEM

TECHNICAL FIELD

The present invention relates to the field of obtaining a combustible gas chosen from methane, methanol, dimethyl ether (DME) or diesel by heterogeneous catalysis.

The production processes according to the invention comprise a step of high-temperature water electrolysis (HTE for "High Temperature Electrolysis" or HTSE for "High Temperature Steam Electrolysis") or a step known as co-electrolysis of water and carbon dioxide $CO_2$ at high temperature and a step of manufacturing combustible gas by catalytic reaction.

The invention relates more particularly to a novel design of reactor whose pressure chamber houses both a high-temperature electrolysis reactor, or electrolyzer (HTE), with a stack of elemental electrolysis cells to produce either hydrogen or a "syngas" (an $H_2$+CO mixture) from steam $H_2O$ and carbon dioxide $CO_2$ and at least one catalyst arranged downstream of the electrolyzer outlet to convert via heterogeneous catalysis into desired combustible gas the syngas obtained previously either directly from the electrolysis reactor or indirectly by mixing the hydrogen produced with carbon dioxide $CO_2$ injected into the chamber.

PRIOR ART

Among the bulk energy storage solutions already envisaged, hydraulic storage is already widespread. The remaining capacities for this type of storage risk being rapidly saturated. In addition, hydraulic systems require particular geographic and geological conditions and may as a result prove to be rather expensive. Given the future storage problems, hydraulic storage can therefore be only a partial solution.

An alternative storage solution has also been envisaged: this is compressed air storage (CAES, the abbreviation for "Compressed Air Energy Storage"). According to this technology, it is envisaged to store compressed air produced with electricity in underground cavities. These cavities also demand specific geographical characteristics, such as saline cavities. However, the yield of this storage solution is unsatisfactory.

Finally, hydrogen is announced as an energy vector that is susceptible to be capable of bulk storage of electricity in certain configurations: mention may be made here of the project already carried out in *Corsica* under the acronym MYRTE (acronym for Mission hYdrogène Renouvelable pour l'Intègration au Rèseau Electrique) at the Applicant's initiative.

However, all these bulk energy storage solutions require the development of extensive infrastructures (hydraulic-specific sites, underground cavities, hydrogen storage systems). This is why, more recently, bulk energy storage by conversion of renewable electricity into chemical energy via the production of synthetic fuel has made significant inroads, representing a storage alternative of great potential. Mention may be made here of patent application US 2009/0289227 which mentions technical conversion solutions.

Moreover, reducing the emissions of carbon dioxide $CO_2$ resulting from the use of fossil energies, upgrading as much as possible the $CO_2$ derived from the use of these energies rather than storing it for an indefinite period, using on demand electricity derived from "decarbonized" energy sources, especially during periods of over production, converting this electricity into a storable product that may make it possible to produce electricity on demand during periods of production deficit without having to resort to the use of high-carbon energies are all objectives to be achieved for the sake of global efficiency.

The manufacture of a combustible syngas from a mixture of steam and carbon dioxide $CO_2$, by means of decarbonized electricity, satisfies these objectives.

The electrolysis of steam $H_2O$ to produce hydrogen $H_2$ and/or the co-electrolysis of $H_2O+CO_2$ at high temperature in a solid oxide electrolyzer is one of the possibilities. The reactions for the electrolysis of steam (I) and for the co-electrolysis of $H_2O+CO_2$ (II) take place according to the following equations:

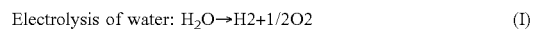

Electrolysis of water: $H_2O \rightarrow H2+1/2 O2$ (I)

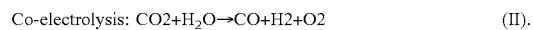

Co-electrolysis: $CO2+H_2O \rightarrow CO+H2+O2$ (II).

Thus, the electrolysis of steam $H_2O$ allows a "direct" manufacture of combustible gas by heterogeneous catalysis by injection of a mixture of hydrogen $H_2$ produced via electrolysis (I) and of carbon dioxide $CO_2$ into a catalyzer.

The co-electrolysis of $H_2O+CO_2$ allows an "indirect" manufacture of combustible gas from the syngas ($H_2$+CO) produced via co-electrolysis (II).

The combustible gas thus manufactured may be a hydrocarbon and especially methane, the main component of natural gas.

The production of synthetic natural gas gives the possibility of immediately using all the existing infrastructures developed for this energy: transportation and distribution networks, storage capacities, electricity production systems, etc. In addition, it also emerges that the carbon balance for this production may be zero, or even negative, since the electricity used would be of decarbonized origin and the $CO_2$ would be derived from systems using fossil energies that would have been taken up beforehand.

To perform the electrolysis of water (I), it is advantageous to perform it at high temperature typically between 600 and 950° C., since part of the energy required for the reaction may be provided by heat, which is less expensive than electricity, and the activation of the reaction is more efficient at high temperature and does not require a catalyst. To perform high-temperature electrolysis, it is known practice to use an electrolyzer of SOEC type (acronym for "Solid Oxide Electrolyte Cell"), consisting of a stack of elementary units each comprising a solid oxide electrolysis cell, consisting of three superposed anode/electrolyte/cathode layers, and of interconnecting plates made of metal alloys also known as bipolar plates, or interconnectors. The function of interconnectors is to ensure both the passage of the electrical current and the circulation of gases in the region of each cell (steam injected, hydrogen and oxygen extracted in an HTE electrolyzer; air and hydrogen injected and water extracted in an SOFC cell) and to separate the anode and cathode compartments which are the compartments for gas circulation on the anode side and the cathode side, respectively, of the cells. To perform high-temperature steam electrolysis HTE, steam $H_2O$ is injected into the cathode compartment. Under the effect of the current applied to the cell, the dissociation of the water molecules in vapor form takes place at the interface between the hydrogen electrode (cathode) and the electrolyte: this dissociation produces hydrogen gas $H_2$ and oxygen ions. The dihydrogen is collected and removed at the hydrogen compartment outlet. The oxygen ions $O^{2-}$ migrate toward the electrolyte and recombine as dioxygen at the interface between the electrolyte and the oxygen electrode (anode).

The co-electrolysis of steam and $CO_2$ (II) potentially offers the same energy and economic advantages as those described above for the electrolysis of steam (reaction (I)) without the drawback of having to perform intermediate condensation between the electrolysis of water and the electrolysis of $CO_2$. Its advantage lies in the possibility of performing the co-electrolysis reaction (II) in the same reactor by maintaining the reactor in a temperature range in the region of 800° C. Specifically, at this temperature, the voltages required for the reduction of $CO_2$ to CO and of $H_2O$ to $H_2$ are virtually identical. By way of example, the abandon voltages, i.e. the electrical voltages obtained without electrical current but solely by means of the different gases on either side of a cell, for a mixture of 90% oxidized species and 10% reduced species at 800° C., are, respectively, equal to 0.852 V for the $H_2O$, $H_2/O_2$ couples and 0.844 V for the $CO_2$, $CO/O_2$ couples.

Furthermore, high-temperature co-electrolysis has the same energy advantage as steam electrolysis between 750 and 900° C. relative to low-temperature water electrolysis. Specifically, the energy required for the dissociation of $H_2O$ molecules is reduced by the vaporization energy. Moreover, the kinetics of the electrolysis reactions of $H_2O$ and $CO_2$ are highly thermally activated and follow an Arrhenius law with activation energies of the order of 120 kj/mol. Consequently, the efficiency of the reactions improves greatly when the temperature is increased. The higher electrochemical activity at high temperature also makes it possible to dispense with expensive catalyst, such as platinum required at lower temperatures. In addition, the production of syngas in the cathode compartment of the co-electrolysis reactor is accompanied by a production of oxygen in the anode compartment, which may be upgraded thereafter, for example for the oxycombustion of natural gas.

That being said, although the high-temperature co-electrolysis (II) as envisaged offers the abovementioned advantages, namely the investment of a single electrolysis reactor, thermal coupling between the various reactions, it has the drawback of not making it possible to obtain a variable $H_2/CO$ ratio in the mixed gas at the reactor outlet. In other words, when co-electrolysis is performed, a desired outlet $H_2/CO$ ratio imposes a given inlet $H_2O/CO_2$ ratio. Specifically, operation close to the thermo-neutral operating point sets the voltage to be applied to the electrolyzer. Thus, for a desired outlet $H_2/CO$ ratio with a degree of water conversion close to 100%, the inlet $CO_2$ and $H_2O$ rates and compositions must necessarily be determined.

However, each syngas intended to produce a combustible gas requires a given $H_2/CO$ ratio as a function of the targeted fuel. Similarly, the direct manufacture of combustible gas requires a given $CO_2/H_2$ ratio as a function of the targeted fuel.

Table 1 below thus illustrates the ratios required as a function of processes for synthesizing different fuels:

TABLE 1

| SYNTHETIC PROCESS | COMBUSTIBLE PRODUCT OBTAINED | $H_2$/CO RATIO REQUIRED | $CO_2/H_2$ RATIO REQUIRED |
|---|---|---|---|
| Synthesis of methane | Natural gas | 1/3 | 1/4 |
| Synthesis of methanol | Methanol | 1/2 | 1/3 |
| Synthesis of dimethyl ether (DME) | DME | 1/1 | 1/2 |
| Fischer-Tropsch synthesis | Diesel | 1/2 | 1/3 |

The Applicant proposed in the patent application filed on Dec. 17, 2012 under the number FR 12 62174 a novel co-electrolysis process and reactor for obtaining at the outlet a variable $H_2/CO$ ratio and thus a syngas whose composition is adapted to produce the desired combustible gas.

Moreover, the operating point adopted for an electrolysis or co-electrolysis reactor also sets the thermal conditions in the electrolysis reactor. Specifically, for electrolyses performed at high temperature, the energy ΔH required for dissociation of the inlet molecule ($H_2O$ or $CO_2$) may be provided in electrical and/or heat form. The thermal energy provided Q is then defined as a function of the voltage U at the terminals of each electrolysis cell by the relationship:

$$Q = \frac{I}{2F}\Delta H - U \cdot I,$$

in which U is the electrical voltage, I is the electrical current and F is the Faraday constant. Thus, three operating regimes are defined, corresponding to three different thermal modes for the stack of electrolysis cells:

the "autothermal" mode in which the imposed voltage Uimp is equal to ΔH/2F. The heat consumed by the dissociation reaction is completely compensated for by the various electrical resistances of the electrolyzer (irreversibilities). The electrolysis reactor (electrolyzer) does not require any particular thermal management, while at the same time remaining temperature-stable;

the "endothermic" mode in which the imposed voltage Uimp is less than ΔH/2F. The electrolyzer consumes more heat than the electrical losses therein. This required heat must thus be supplied thereto by another means, otherwise its temperature will irremediably drop;

the "exothermic" mode in which the imposed voltage Uimp is greater than ΔH/2F. The electrolysis then consumes less heat than the electrical losses via the Joule effect. This evolution of heat in the electrolyzer must then be evacuated by another means, otherwise its temperature will prohibitively increase.

The endothermic mode requires less consumption of electricity: there is thus little production and heat needs to be supplied to the electrolysis reactor. The advantage of this endothermic mode lies in the availability of an inexpensive source of heat. Everything then depends on the nature and on the temperature of this heat source.

In contrast, the exothermic mode requires a larger consumption of electricity: there is thus substantial production, but the electrolysis reactor must be cooled, which may be very expensive. The advantage of this exothermic mode then depends greatly on the cost of the electricity and the use of the excess heat.

Thus, the heat management of an electrolysis or co-electrolysis reactor is an important factor to be taken into consideration.

In addition, the transportation, storage and use of hydrogen require its pressurization. It is already known practice, instead of compressing the hydrogen produced, which entails a considerable cost, to perform the electrolysis of water directly using steam under pressure, the water then being compressed into liquid form beforehand, which is much less expensive.

Various processes for obtaining a combustible gas by heterogeneous catalysis either directly using a mixture of $H_2$ and carbon dioxide $CO_2$, or indirectly using a syngas ($H_2$+CO) have already been studied.

In particular, the hydrogenation of $CO_2$ to methane is an industrial process that has been studied at each energy shock, either to produce synthetic methane from pure $CO_2$ and $H_2$, or in coal gasification plants with more complicated gases and conditions (Fischer-Tropsch process).

For the methanation process, two routes are possible and have been more or less extensively studied in the prior art.

The first route is the direct route, with a single reaction according to the following equation:

$$CO_2 + 4H_2 \rightarrow CH_4 + 2H_2O$$

The second route is the indirect route, with a two-step reaction according to the following equations:

$$CO_2 + H_2 \rightarrow CO + H_2O$$

$$CO + 3H_2 \rightarrow CH_4 + H_2O.$$

As demonstrated by the authors of the publication [1] (see especially FIGS. 3 and 4), methanation reactions are favored at high pressure and at low temperature according to the Le Chatelier law. Specifically, the thermodynamic calculations indicated in [1] indicate a theoretical conversion of 100% of $CO_2$ into $CH_4$ at less than 150° C. as opposed to 83% at 400° C. However, it is also indicated that a minimum temperature and an optimum gas rate is to be adjusted in order to ensure sufficient kinetics. The optimum temperature at which the methanation should be performed is thus a compromise between the desired degree of conversion of $CO_2$ and the desired reaction kinetics.

The catalysts used for methanation are generally based on nickel supported on a zirconium oxide ($ZrO_2$) or based on nickel (Ni) supported on an aluminum oxide ($Al_2O_3$). Publication [1] highlighted the high catalytic activity for a catalyst based on nickel (Ni) supported on mixed oxides of cerium (Ce) and zirconium of formula Ce0.72Zr0.28O2. Similarly, publication [2] showed, for a methanation at a pressure of 30 bar, the excellent catalytic activity of a bimetallic catalyst based on nickel (Ni) and iron (Fe) supported on an aluminum oxide ($Al_2O_3$) of formula Ni—Fe/γ-$Al_2O_3$.

Several types of reactors have already been envisaged for performing methanation.

Mention may be made first of fixed-bed reactors in which the solid catalyst is integrated in the form of grains or pellets. The drawback of reactors of this type is that the heat management is difficult to perform for exothermic reactions such as methanation.

Mention may also be made of reactors with structured channels such as multitubular reactors, monolithic reactors and plate reactors, in which the solid catalyst is generally deposited in the form of a coating in the reactive channels. These reactors are well suited to a methanation reaction which requires good heat management. They are generally more expensive.

Finally, reactors of entrained or fluidized-bed type in which the catalyst to be fluidized is in powder form. These reactors are well suited to reactions with very large volumes of reagents. Furthermore, fluidization of the catalyst allows very good thermal homogenization of the mixture of reagents in the reactor and thus better heat control.

Irrespective of the direct or indirect route, the solid catalyst, or the type of reactor used to date, methanation remains an expensive process with a yield that is still to be improved, especially due to the subsequent compression of the methane obtained, which is necessary for its storage and/or transportation and due to the separate production of the hydrogen required, in particular by HTE electrolysis or high-temperature co-electrolysis. The effective coupling to date, between methanation and electrolysis, is far from having been achieved.

Patent application FR2931168 describes an electrolyzer of proton type, i.e. with circulation of protons H+ in the electrolyte, into which water $H_2O$ is introduced at the anode and $CO_2$ or CO is introduced at the cathode, in order to form methane or other fuels. The type of materials used is far from being tried and tested. In addition, the efficiency of methanation in such a proton electrolyzer is far from having been proven.

There is thus a need to improve the methanation process especially in order to lower its investment and production cost and in order to improve its yield.

More generally, there is a need to improve the known synthetic processes for obtaining a combustible gas chosen from methane, methanol and DME, especially in order to lower their investment and production costs and in order to improve their yields.

The aim of the invention is to at least partly satisfy these needs.

DESCRIPTION OF THE INVENTION

To do this, according to one of its aspects, and in a first alternative, the invention relates to a process for obtaining a combustible gas chosen from methane, methanol, dimethyl ether (DME) and diesel by heterogeneous catalysis, comprising the following steps:

a/ a step of high-temperature electrolysis of steam $H_2O$ performed in an electrolysis reactor housed in a leaktight chamber maintained at a given pressure, in which step a/ each cathode of the reactor is fed with steam at the given pressure;

b/ a step of catalytic conversion performed in at least one reaction zone placed at a distance from and radially to the electrolysis reactor in the same chamber under pressure and containing at least one solid conversion catalyst, step b/ being performed using hydrogen $H_2$ produced during the electrolysis step a/ and carbon dioxide $CO_2$ injected into the space between the electrolysis reactor and the radial reaction zone;

c/ a step of recovery of the combustible gas produced and of the steam not converted in step a/ and produced in step b/, in the space between said radial reaction zone and the wall(s) delimiting the chamber.

According to a second alternative, the invention relates to a process for obtaining a combustible gas chosen from methane, methanol, dimethyl ether (DME) and diesel by heterogeneous catalysis, comprising the following steps:

a'/ a step of high-temperature co-electrolysis of steam $H_2O$ and carbon dioxide $CO_2$ performed in a co-electrolysis reactor housed in a leaktight chamber maintained at a given pressure; in which step a'/ each cathode of the reactor is fed with steam $H_2O$ and carbon dioxide $CO_2$ at the given pressure;

b'/ a step of catalytic conversion being performed in at least one reaction zone placed at a distance from and radially to the co-electrolysis reactor in the same chamber under pressure and containing at least one solid conversion catalyst, step b'/ being performed using hydrogen $H_2$ and carbon monoxide CO produced during the co-electrolysis step a'/;

c'/ a step of recovering the combustible gas produced and the steam not converted in step a'/ and produced in step b'/, in the space between said radial reaction zone and the wall(s) delimiting the chamber.

It is pointed out that, in the context of the invention, the high temperatures of the electrolysis step a) or co-electrolysis step a') should not be confused with the low temperatures at which an electrolysis of alkaline type is performed.

In the context of the invention, the term "leaktight chamber under a given pressure" should be understood here to mean a chamber that is leaktight with respect to the external atmosphere and whose interior is maintained at a pressure above atmospheric pressure.

According to an advantageous embodiment, the reaction zone consists of a porous partition containing the solid conversion catalyst.

The term "porous partition" means an assembly formed from one or more walls whose overall porosity allows the passage of the gases present in the chamber, i.e. the methane formed in the partition and steam. The assembly may thus consist of at least two grilles, grates, metal sheets or two substrates made of highly porous ceramic and of which the space separating them contains at least one solid conversion catalyst according to step b/ or b'/.

The term "reaction zone placed at a distance from" and "porous partition placed at a distance from" means an arrangement with a sufficient space between the zone (porous partition and the electrolysis/co-electrolysis reactor so that the temperature of the gases reaches a range of values suitable for performing step b) or b'). Typically, the optimum temperature for performing the methanation step b) or b') is about 400° C., and a sufficient space is thus provided for the $H_2$ produced with the $CO_2$ injected or the $H_2$+CO mixture produced in the region of 800 to 850° C. to reach a temperature of about 400° C. when it enters the reaction zone (porous partition).

Step b/ or b'/ is preferably performed with the radial reaction zone closed on itself, being arranged concentrically around the electrolysis or co-electrolysis reactor, respectively.

Step a/ or a'/ is advantageously performed at temperatures of between 600° C. and 1000° C., preferably between 650° C. and 850° C.; more preferably between 700 and 800° C.

Step b/ or b'/ is advantageously performed at temperatures of between 250° C. and 500° C., preferably between 300° C. and 400° C.

Step a/ or a'/ is preferably performed at pressures of between 0 and 100 bar, preferably between 4 and 80 bar, i.e. a range between the pressure in a medium-pressure distribution network (4 bar) and that in natural gas pipelines (80 bar).

According to an advantageous embodiment, the walls delimiting the chamber are cooled to a temperature below the saturation temperature of water at the given pressure of the chamber, such that step c/ or c'/ consists of a separation of the combustible gas from the water condensed in the chamber, followed by a recovery of the combustible gas separated out and of the condensed water by gravity on the bottom of the chamber.

The process advantageously constitutes a methanation process. In such a process, advantageously, the given pressure of the chamber and the operating pressure of the electrolysis or co-electrolysis reactor is equal to about 30 bar, the temperature for performing step a/ or a'/ being maintained equal to about 800° C., the temperature in the radial reaction zone being maintained equal to about 400° C., the temperature of the walls delimiting the chamber being maintained below 230° C.

In another of its aspects, the invention also relates to a reactor for obtaining a combustible gas chosen from methane, methanol, dimethyl ether (DME) and diesel by heterogeneous catalysis, comprising:

a leaktight chamber capable of being placed under a given pressure;

a reactor either for the high-temperature electrolysis of steam or for the high-temperature co-electrolysis of steam and carbon dioxide, comprising a stack of elemental electrolysis cells of SOEC type each formed from a cathode, an anode and an electrolyte intercalated between the cathode and the anode, and a plurality of electrical and fluid interconnectors each arranged between two adjacent elemental cells with one of its faces in electrical contact with the anode of one of the two elemental cells and the other of its faces in electrical contact with the cathode of the other of the two elemental cells, the electrolysis or co-electrolysis reactor being housed in the chamber and the outlet of the cathodes emerging inside the chamber;

at least one porous partition placed at a distance from and radially to the electrolysis or co-electrolysis reactor in the chamber and containing at least one solid catalyst for converting syngas ($H_2$+CO or $H_2$+$CO_2$) into combustible gas;

at least one tube for feeding steam under pressure and, where appropriate, carbon dioxide to the cathodes of the electrolysis or co-electrolysis reactor, where appropriate, at least one tube for injecting carbon dioxide of the space between the electrolysis reactor and the porous partition;

at least one tube for recovering combustible gas and/or steam, where appropriate, at least one tube for recovering water condensed on the walls delimiting the chamber, each tube passing through a wall delimiting the chamber.

It is pointed out here that the electrical and fluid interconnection devices, also known as interconnectors or interconnection plates, are devices which provide connection in series from an electrical point of view of each electrolysis cell in the stack of HTE reactors and in parallel from a fluid point of view, thus combining the production of each of the cells. The interconnectors thus ensure the functions of bringing and collecting current and delimit gas circulation (distribution and/or collection) compartments.

The electrolysis cells are advantageously of cathode-supported type. In the context of the invention, the term "cathode-supported cell" means herein the definition already given in the field of high-temperature water electrolysis HTE and referred to by the acronym CSC, i.e. a cell in which the electrolyte and the oxygen electrode (anode) are arranged on the hydrogen or carbon monoxide electrode (cathode), which is thicker and thus serves as a support.

According to an advantageous embodiment, the porous partition is closed on itself, being arranged concentrically around the electrolysis or co-electrolysis reactor. The porous partition preferably consists of two porous metal walls, the space separating them being at least partially filled with a conversion catalyst in the form of powder or granulates. The two metal walls each preferably consist of a sheet perforated with a plurality of holes regularly spaced both along the height and along the length of the partition.

The solid conversion catalyst is preferably based on nickel (Ni) supported on a zirconium oxide ($ZrO_2$), or based on nickel (Ni) supported on an aluminum oxide ($Al_2O_3$), or bimetallic based on nickel (Ni) and iron (Fe) supported on an aluminum oxide ($Al_2O_3$), preferably Ni—Fe/$\gamma$-$Al_2O_3$, or based on nickel (Ni) supported on mixed oxides of cerium (Ce) and zirconium, preferably $Ce_{0.72}Zr_{0.28}O_2$.

The porous partition advantageously comprises, in the solid catalyst, part of the cooling circuit capable of cooling the catalytic reaction between the hydrogen and carbon monoxide produced upstream in the co-electrolysis reactor or between the hydrogen produced upstream in the electrolysis reactor and carbon dioxide injected into the space between the porous partition and the electrolysis reactor.

The feed tube is preferably partly wound on itself close to the electrolysis or co-electrolysis reactor to heat the steam under pressure and, where appropriate, the carbon dioxide before feeding the cathodes.

According to an advantageous embodiment variant, the reactor comprises a tube for recovering the hydrogen and, where appropriate, the carbon monoxide produced at the cathodes, the recovery tube being wound on itself forming a circle and being pierced with a plurality of holes regularly distributed along the circle to homogeneously diffuse the hydrogen and, where appropriate, the carbon monoxide into the space between the electrolysis or co-electrolysis reactor and the porous partition arranged concentrically.

The carbon dioxide injection tube is preferably wound on itself forming a circle and pierced with a plurality of holes regularly distributed along the circle to homogeneously diffuse the carbon dioxide into the space between the electrolysis or co-electrolysis reactor and the porous partition arranged concentrically.

According to an advantageous embodiment variant, the leaktight chamber comprises a side envelope, a lid and a base assembled with the envelope in a leaktight manner, and a first support for supporting both the electrolysis or co-electrolysis reactor and the porous partition so as to place them at a distance from the base and from the lid of the chamber.

Preferably, the reactor comprises a second support, fixed onto the first support, for supporting only the electrolysis or co-electrolysis reactor so as to place it facing the central portion of the porous partition, preferably halfway up the porous partition.

According to an advantageous embodiment variant, the side envelope comprises part of a cooling circuit at a temperature below the saturation temperature of water at the given pressure.

The base of the leaktight chamber advantageously constitutes a basin for recovering the water condensed on the lid and/or the side envelope and/or the base.

According to another of its aspects, the invention relates to a system comprising:
a reactor that has just been described;
a heat exchanger forming a steam generator for vaporizing liquid water at the given pressure, the exchanger being placed outside the chamber.

In such a system, part of the secondary circuit of the exchanger advantageously comprises the tube for recovering the water condensed in the base.

The cooling circuit of the porous partition advantageously constitutes the primary circuit of the heat exchanger for vaporizing the liquid water at the given pressure.

In yet another of its aspects, the invention relates to a process for operating a co-electrolysis reactor described above, according to which steam is fed and distributed to the cathode of one of the two adjacent elemental cells and carbon dioxide is fed and distributed to the cathode of the other of the two elemental cells.

According to an advantageous embodiment, an operating regime in exothermic mode is defined for the electrolysis of steam at the cathode of one of the two adjacent elemental cells and an operating regime in endothermic mode is simultaneously performed for the electrolysis of carbon dioxide at the cathode of the other of the two adjacent elemental cells, the heat evolved by the electrolysis of steam being capable of at least partly providing the heat required for the electrolysis of the carbon dioxide.

Alternatively, an operating regime in exothermic mode is defined for the electrolysis of carbon dioxide at the cathode of one of the two adjacent elemental cells and an operating regime in endothermic mode is simultaneously performed for the electrolysis of steam of the other of the two adjacent elemental cells, the heat evolved by the electrolysis of the carbon dioxide being capable of at least partly providing the heat required for the electrolysis of the steam.

The invention also relates to the use of the reactor described or of the system described as a methanation reactor.

The invention also relates to the use of the reactor described as a fuel cell and catalytic reforming reactor, the chamber not being under pressure, the combustible gas recovery tube constituting a combustible gas feed tube and the stacked-cell electrolysis or co-electrolysis reactor constituting an SOFC fuel cell.

In other words, the conversion processes according to the invention, in particular for methanation, consist essentially in injecting steam under pressure into a chamber, electrolyzing the steam $H_2O$ or co-electrolyzing the steam $H_2O$ and carbon dioxide $CO_2$ at high temperature and performing catalytic conversion into combustible gas in the same chamber maintained under pressure, by placing the reaction zone at a sufficient distance from the electrolysis or co-electrolysis reactor to obtain an optimum gas temperature range for the catalytic conversion. The process according to the invention is advantageously performed by means of the reactor according to the invention.

In other words, the invention makes it possible to produce methane at a high-temperature water electrolysis pressure that is already tried and tested, typically 30 bar, without having to invest specifically in one or more items of equipment dedicated to pressurization since the leaktight chamber under pressure according to the invention serves both as a chamber for the catalytic conversion and for the electrolysis/co-electrolysis.

The co-electrolysis of steam and carbon dioxide may advantageously be performed in the stack reactor according to the teaching of the abovementioned application FR 12 62174: steam is fed and distributed to the cathode of one of the two adjacent elemental cells and carbon dioxide is fed and distributed to the cathode of the other of the two elemental cells. This makes it possible to vary at will the $H_2$/CO ratio obtained at the outlet before mixing it to constitute the syngas converted into combustible gas in the chamber, and to facilitate the thermal management of the stack of electrolysis cells irrespective of the operating mode (endothermic or exothermic mode), and to do so reversibly as a function of the current cost.

The advantages of electrolysis of steam under pressure or of co-electrolysis of steam and carbon dioxide combined with a catalytic conversion into combustible gas in the same chamber maintained under pressure, in accordance with the invention, are manifold. Among these, mention may be made of:

- use of a single machine with a single chamber to perform both the electrolysis of steam or the co-electrolysis of steam and $CO_2$ and catalytic conversion into combustible gas, more particularly methanation, which makes it possible to limit the investment;
- strong integration of the thermal management between electrolysis/co-electrolysis and catalytic conversion in the same chamber when compared with the known processes requiring the sequential use of at least two different reactors;
- dimensioning of the pressure resistance for a single chamber both for electrolysis/co-electrolysis and for catalytic conversion (methanation). In particular, the catalytic conversion may be performed at high pressure required for electrolysis/co-electrolysis without the need to invest in an additional chamber. The wall(s) constituting the porous partition placed at a distance from the electrolysis or co-electrolysis reactor, for performing step b/ or b'/, in particular methanation, may be of very simple design and of low cost;
- performing catalytic conversion, in particular methanation, under pressure, which allows operation of the solid catalyst over a wide temperature range and thus introduces a certain level of flexibility into the thermal management. This also makes it possible to perform the catalytic conversion at high pressure, typically the pressure usually encountered in methane gas pipelines, i.e. at 80 bar, without having to make any specific investment. In particular, any compression of the combustible gas, such as methane $CH_4$, leaving the chamber according to the invention may thus be dispensed with;
- direct conveying of the methane obtained into the gas network under pressure if less than 10% unconverted hydrogen remains;
- possible elimination of any detrimental thermal gradient in the porous partition, by means of the possible concentric arrangement of the porous partition closed on itself around and at a distance from the electrolysis/co-electrolysis reactor, the path of the gas to be converted in the catalyst may be relatively short, even for a large amount of catalyst, which is favorable for the thermal management of the catalytic conversion, such as methanation, which takes place over the entire circumference of the partition. The thickness of the partition containing the solid catalyst may then be relatively low with respect to its other dimensions;
- better management of the risks associated with the use of the chamber under pressure when compared with the HTE electrolyzers according to the prior art, due firstly to the reduction in the volume of gas required for the same thermal gradient between the electrolysis reactor and the walls delimiting the chamber and secondly to the heat shield function at lower temperature imparted to the porous partition, typically at 400° C. for methanation, with respect to the walls of the chamber whose temperature it is desired to control;
- additional flexibility for the thermal management of the overall reactor according to the invention by means of the heating brought about by the introduction of the syngas to the inner wall of the porous partition and which is located in an already hot space of the chamber;
- flexibility of use of the reactor according to the invention since, firstly, it is possible to perform the methanation either via the direct route or via the indirect route by injecting $CO_2$ and, secondly its operation may be reversed by injecting methane $CH_4$, the partition containing the solid catalyst then functioning as a catalytic pre-reformer and the electrolysis reactor of SOEC type functioning as an SOFC fuel cell; in other words, in the context of the invention, the inversion leads to using the partition with the solid catalyst as a reformer and the SOEC electrolysis reactor as an SOFC fuel cell so as to produce electrical current;
- less consumption of water and less investment in water treatment equipment when compared with sequential HTE electrolysis and methanation according to the prior art. Thus, maintaining the walls delimiting the chamber at a temperature below the water saturation temperature at the given pressure makes it possible to be able to separate the methane produced and the water not converted by condensing this water on said walls. The water thus condensed may then be reinjected into the steam production device of the system (vaporization heat exchanger). Consequently, when compared with a system according to the prior art with the methanation reactor and the water electrolysis reactor separated, investment in a pressurized condenser to obtain dry methane is avoided;
- depending on the application intended for the use of the methane obtained according to the invention, if the pressure of the chamber and thus of the methane obtained is too high, possibility of expanding the methane and, as a result, in participating in the cooling of the chamber;
- possibility of liquefying the methane under very high pressure obtained according to the invention by successive expansions for its transportation.

DETAILED DESCRIPTION

Figure 2:
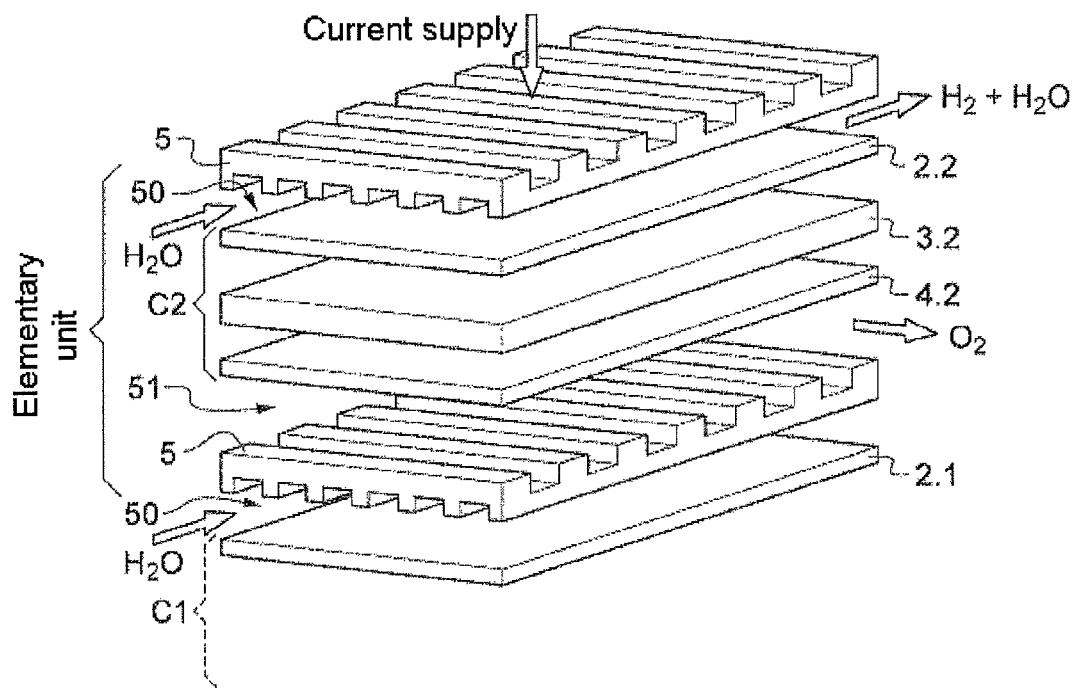
Figure 3:
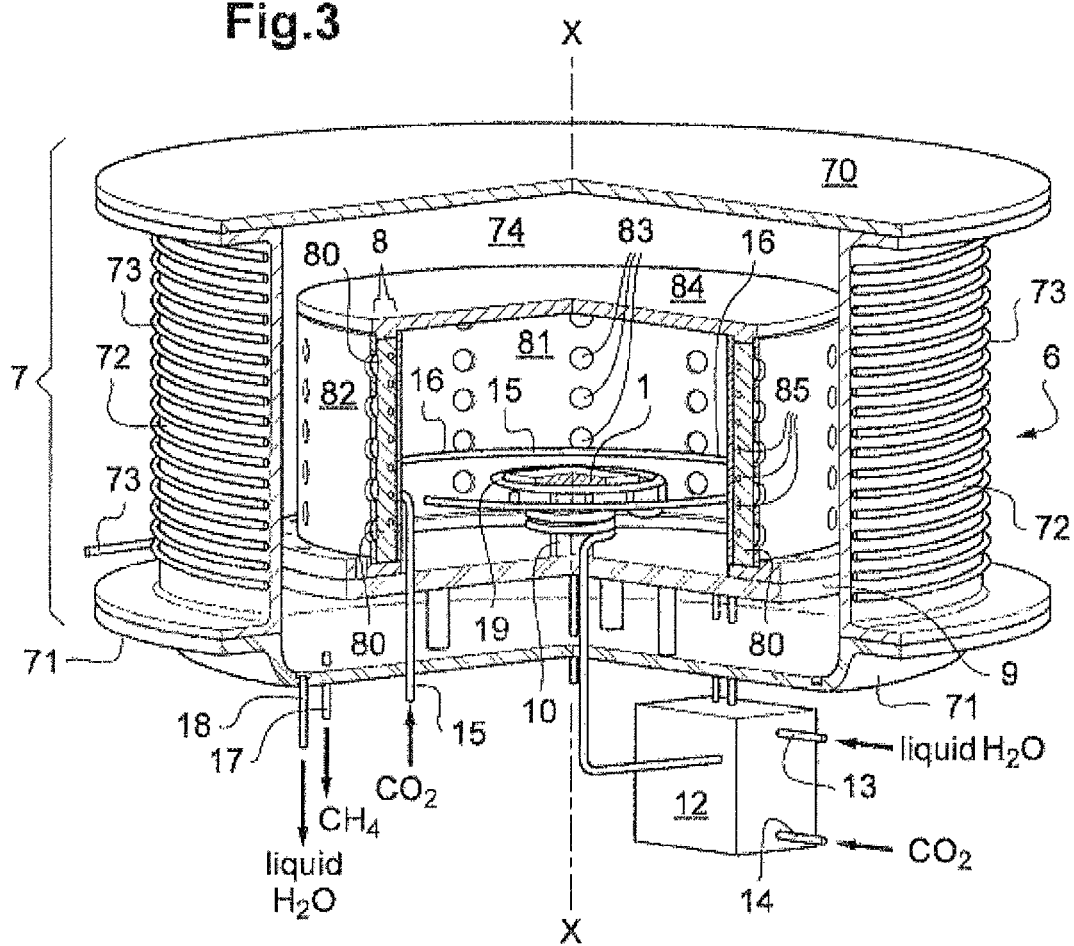
Figure 4:
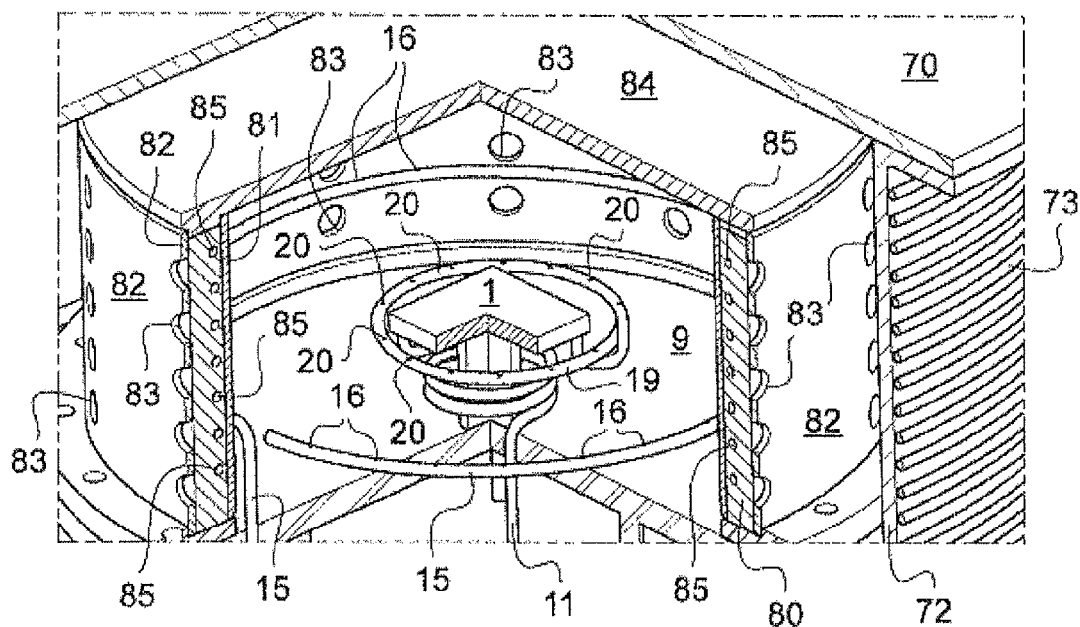
Figure 5:
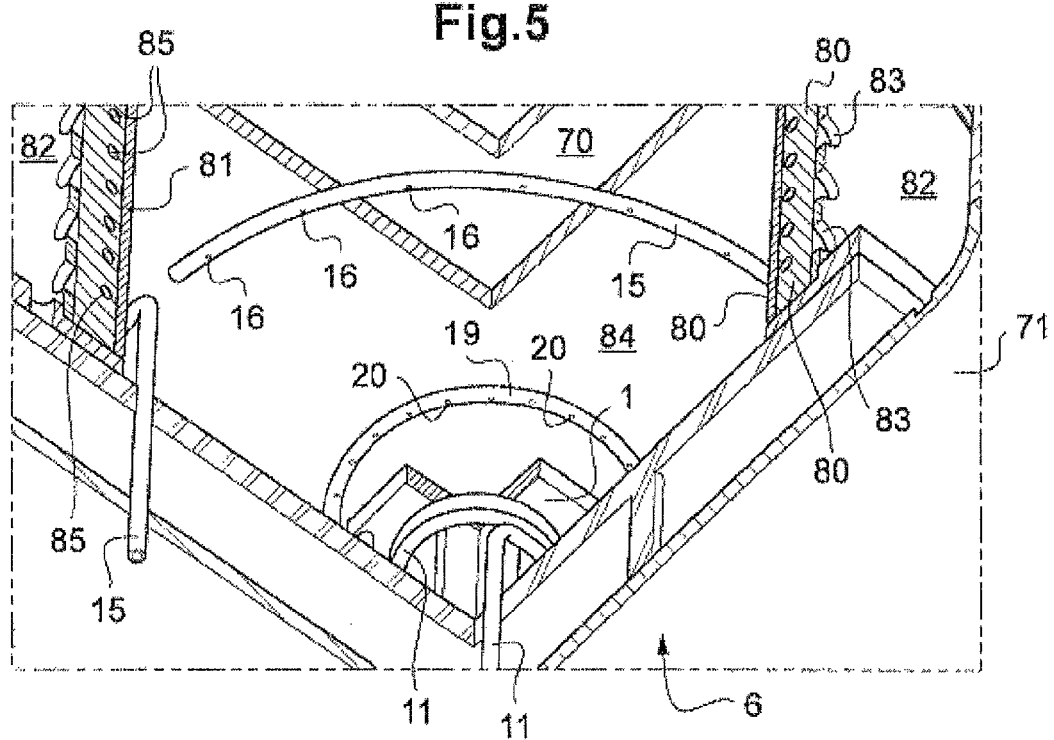

Other advantages and characteristics of the invention will emerge more clearly on reading the detailed description of examples of implementation of the invention given as non-limiting illustrations with reference to the following figures, among which:

FIG. 1 is a schematic view showing the operating principle of a high-temperature water electrolyzer;

FIG. 2 is an exploded schematic view of part of a high-temperature steam electrolyzer comprising interconnectors, FIG. 3 is a view in perspective partially cutaway of a reactor according to the invention performing in the same chamber under pressure either high-temperature electrolysis of steam $H_2O$ or high-temperature co-electrolysis of steam $H_2O$ and of carbon dioxide $CO_2$ and methanation using the gas(es) produced by the electrolysis or the co-electrolysis, FIG. 4 is a detailed view in perspective partially cutaway of the reactor according to FIG. 3, FIG. 5 is another detailed view in perspective partially cutaway of the reactor according to FIG. 3.

Throughout the present application, the terms "vertical", "lower", "upper", "bottom", "top", "below" and "above" are to be taken by reference relative to a reactor for obtaining a combustible gas with its chamber under pressure such that they are in vertical operating configuration. Thus, in an operating configuration, the chamber is arranged vertically with its base at the bottom and the electrolysis or co-electrolysis reactor is arranged with its cells horizontal on its dedicated support.

Similarly, in the assembly of the present application, the terms "inlet", "outlet", "downstream" and "upstream" are to be understood with reference to the direction of circulation of the gases from their entry into the HTE electrolysis or co-electrolysis reactor or into the leaktight chamber under pressure up to their exit therefrom.

It is pointed out that, in all the FIGS. 1 to 5, the symbols and arrows for feeding steam $H_2O$, for distributing and recovering dihydrogen $H_2$ and oxygen $O_2$, and current, carbon dioxide $CO_2$, for distributing and recovering carbon monoxide CO and oxygen $O_2$ and current, and methane $CH_4$ are shown for the purposes of clarity and precision, to illustrate the functioning of a steam electrolysis or simultaneous steam and carbon dioxide co-electrolysis reactor that are known and of a methanation reactor according to the invention.

It is also pointed out that, in FIGS. 3 to 5 relating to a methanation reactor according to the invention, the recovery of oxygen $O_2$ at the electrolyzer or co-electrolyzer outlet is not shown, for the purposes of clarity.

It is also pointed out that all the electrolyzers or co-electrolyzers described are of the solid oxide type (SOEC, Solid Oxide Electrolyte Cell) operating at high temperature. Thus, all the constituents (anode/electrolyte/cathode) of an electrolysis cell are ceramic.

Such constituents may be those of an SOFC fuel cell. The high operating temperature of an electrolyzer (electrolysis reactor) is typically between 600° C. and 1000° C. Preferably, in the context of the invention, a preferred range between 650 and 850° C. and more preferably between 700 and 800° C. is envisaged.

Typically, the characteristics of an SOEC elemental electrolysis cell in accordance with the invention, of the cathode-supported type (CSC), may be those indicated as follows in table 2 below.

TABLE 2

| Electrolysis cell | Unit | Value |
|---|---|---|
| Cathode 2 | | |
| Constituent material | | Ni-YSZ |
| Thickness | μm | 315 |
| Thermal conductivity | W m$^{-1}$ K$^{-1}$ | 13.1 |
| Electrical conductivity | Ω$^{-1}$ m$^{-1}$ | 10$^5$ |
| Porosity | | 0.37 |
| Permeability | m$^2$ | 10$^{-13}$ |
| Tortuosity | | 4 |
| Current density | A · m$^{-2}$ | 5300 |
| Anode 4 | | |
| Constituent material | | LSM |
| Thickness | μm | 20 |
| Thermal conductivity | W m$^{-1}$ K$^{-1}$ | 9.6 |
| Electrical conductivity | Ω$^{-1}$ m$^{-1}$ | 1 10$^4$ |
| Porosity | | 0.37 |
| Permeability | m$^2$ | 10$^{-13}$ |
| Tortuosity | | |
| Current density | A · m$^{-2}$ | 2000 |
| Electrolyte 3 | | |
| Constituent material | | YSZ |
| Thickness | μm | |
| Resistivity | Ω m | 0.42 |

A water electrolyzer is an electrochemical device for producing hydrogen (and oxygen) under the effect of an electrical current.

In HTE high-temperature electrolyzers, the electrolysis of water at high temperature is performed using steam. The function of an HTE high-temperature electrolyzer is to convert the steam into hydrogen and oxygen according to the following reaction:

$$2H_2O \rightarrow 2H_2 + O_2.$$

This reaction is performed electrochemically in the cells of the electrolyzer. As represented schematically in FIG. 1, each elemental electrolysis cell 1 is formed from a cathode 2 and an anode 4, placed on either side of a solid electrolyte 3. The two electrodes (cathode and anode) 2, 4 are electron conductors, made of porous material, and electrolyte 3 is gas-tight, an electronic insulator and an ion conductor. The electrolyte may in particular be an anionic conductor, more precisely an anionic conductor of $O^{2-}$ ions and the electrolyzer is then referred to as an anionic electrolyzer.

The electrochemical reactions take place at the interface between each of the electron conductors and the ion conductor.

At cathode 2, the half-reaction is as follows:

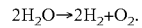

At anode 4, the half-reaction is as follows:

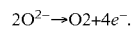

Electrolyte 3 is intercalated between the two electrodes 2, 4 and is the site of migration of the $O^{2-}$ ions under the effect of the electrical field created by the potential difference imposed between anode 4 and cathode 2.

As illustrated in parentheses in FIG. 1, the steam entering the cathode may be accompanied by hydrogen $H_2$ and the hydrogen produced and recovered at the outlet may be accompanied by steam. Similarly, as illustrated with dashed lines, a draining gas, such as air, may also be injected into the inlet to remove the oxygen produced. The injection of a draining gas has the further function of acting as a heat regulator.

An elemental electrolysis reactor consists of an elemental cell as described above, with a cathode 2, an electrolyte 3 and an anode 4 and two monopolar connectors which ensure the electrical, hydraulic and thermal distribution functions.

To increase the flow rates of hydrogen and oxygen produced, it is known practice to stack several elemental electrolysis cells on top of each other, separating them with interconnection devices, usually known as interconnectors or bipolar interconnection plates. The assembly is positioned between two end interconnection plates which support the electrical feeds and gas feeds of the electrolyzer (electrolysis reactor).

A high-temperature water electrolyzer (HTE) thus comprises at least one, generally a plurality of, electrolysis cells stacked on top of each other, each elemental cell being formed from an electrolyte, a cathode and an anode, the electrolyte being intercalated between the anode and the cathode.

The fluid and electrical interconnection devices that are in electrical contact with one or more electrodes generally ensure the functions of conveying and collecting electrical current and delimit one or more gas circulation compartments.

Thus, a "cathode" compartment has the function of distributing electrical current and steam and also recovering hydrogen at the cathode in contact.

An "anode" compartment has the function of distributing electrical current and recovering the oxygen produced at the anode in contact, optionally with the aid of a draining gas.

Satisfactory functioning of an HTE electrolyzer requires:
- good electrical insulation between two adjacent interconnectors in the stack, otherwise the elemental electrolysis cell intercalated between the two interconnectors will be short-circuited,
- good electrical contact and a sufficient contact surface between each cell and interconnector, so as to obtain the lowest ohmic resistance between cell and interconnectors,
- good leaktightness between the two separate compartments, i.e. and cathode, otherwise the gases produced will undergo recombination resulting in a lowering of yield and above all the appearance of hot spots that damage the electrolyzer,
- good distribution of the gases both at the inlet and on recovery of the gases produced, otherwise there will be a loss of yield, non-uniformity of pressure and temperature in the various elemental cells, or even prohibitive degradation of the cells.

FIG. 2 shows an exploded view of elementary units of a high-temperature steam electrolyzer according to the prior art. This HTE electrolyzer comprises a plurality of elemental electrolysis cells C1, C2, of solid oxide type (SOEC) stacked alternately with interconnectors 5. Each cell C1, C2, etc. consists of a cathode 2.1, 2.2, etc. and an anode 4.1, 4.2, between which is placed an electrolyte 3.1, 3.2, etc.

The interconnector 5 is a component made of metal alloy which ensures separation between the cathode compartment 50 and the anode compartment 51, defined by the volumes between the interconnector 5 and the adjacent anode 4.2 and between the interconnector 5 and the adjacent cathode 2.1, respectively. It also ensures the distribution of the gases to the cells. The injection of steam into each elementary unit takes place in the cathode compartment 50. The collection of the hydrogen produced and of the residual steam at the cathode 2.1, 2.2, etc. is performed in the cathode compartment 50 downstream of the cell C1, C2, etc. after dissociation of the steam by the latter. The collection of the oxygen produced at the anode 4.2 is performed in the anode compartment 51 downstream of the cell C1, C2, etc. after dissociation of the steam by the latter.

The interconnector 5 ensures the passage of the current between the cells C1 and C2 by direct contact with the adjacent electrodes, i.e. between the anode 4.2 and the cathode 2.1.

In the high-temperature co-electrolyzers HTE, the high-temperature co-electrolysis is performed using steam and carbon dioxide $CO_2$. The function of an SOEC high-temperature co-electrolyzer is to transform steam and $CO_2$ into hydrogen, carbon monoxide and oxygen according to the following reaction:

$$CO_2 + H_2O \rightarrow CO + H_2 + O_2.$$

A co-electrolyzer 1 may comprise exactly the same solid oxide constituents (SOEC) as an HTE electrolyzer which has just been described. Usually, the steam and carbon dioxide $CO_2$ are mixed before entering the co-electrolyzer and injected simultaneously into each cathode compartment 50.

In order to obtain a variable ratio between the outlet gases produced, $H_2/CO$, irrespective of the exothermic or endothermic mode of operation of a given electrolysis cell, the Applicant proposed in the abovementioned patent application FR 12 62174, a novel process for the simultaneous but separate electrolysis of steam and $CO_2$.

More precisely, the process for the high-temperature co-electrolysis of steam $H_2O$ and carbon dioxide $CO_2$ according to patent application FR 12 62174 is performed with the electrolysis reactor comprising a stack of elemental electrolysis cells of SOEC type (C1, C2, C3) each formed from a cathode 2.1, 2.2, 2.3, an anode 4.1, 4.2, 4.3 and an electrolyte 3.1, 3.2, 3.3, intercalated between the cathode and the anode, and a plurality of electrical and fluidic interconnectors 5 each arranged between two adjacent elemental cells with one of its faces in electrical contact with the anode of one of the two elemental cells and the other of its faces in electrical contact with the cathode of the other of the two elemental cells. Steam is fed and distributed to the cathode 2.1, 2.3 of one (C1 or C3) of the two adjacent elemental cells (C1, C2; C2, C3) and carbon dioxide is fed and distributed to the cathode 2.2 of the other (C2) of the two elemental cells (C1, C2; C2, C3).

In the co-electrolysis reactor according to application FR 12 62174, all the cathode compartments 50 in which circulate the steam $H_2O$ fed in and the hydrogen $H_2$ produced communicate with each other. Similarly, all the cathode compartments 50 in which circulate the carbon dioxide $CO_2$ injected in and the carbon monoxide CO produced communicate with each other, but are completely isolated from the compartments 50 dedicated to the steam $H_2O$ and to the hydrogen $H_2$ produced. Finally, the two simultaneous but separate electrolysis reactions both produce oxygen which is collected by all the anode compartments 51 which communicate with each other, irrespective of the reaction concerned.

At the present time, when it is desired to perform a methanation, two routes are possible. The first is the direct route, with a single reaction according to the following equation:

$$CO_2 + 4H_2 \rightarrow CH_4 + 2H_2O.$$

The second is the indirect route, with a two-step reaction according to the following equations:

$$CO_2 + H_2 \rightarrow CO + H_2O$$

$$CO + 3H2 \rightarrow CH_4 + H_2O.$$

The methanation is performed in a reactor in which the solid reaction catalyst is present.

Hydrogen and, where appropriate, carbon monoxide may be produced beforehand either by HTE electrolysis in an electrolysis reactor 1 described with reference to FIG. 1 to 3, or by high-temperature co-electrolysis also in a co-electrolysis reactor 1 described or in a simultaneous co-electrolysis reactor according to patent application FR 12 62174.

Thus, the overall process involves the sequential use of two separate reactors, that for electrolysis/co-electrolysis and that for methanation, with, as the major related drawbacks, a heavy investment and a high production cost especially due to the thermal decoupling between the two separate reactors and the need to compress at the outlet of the methanation reactor the methane produced so as to be able to transport it either in dedicated natural gas pipelines at a pressure of 80 bar, or in "medium-pressure" distribution networks at 4 bar.

To overcome these drawbacks, the inventors of the present invention thought to integrate a methanation reactor with its solid catalyst and a high-temperature steam electrolyzer (SOEC) or a co-electrolyzer of steam and carbon dioxide $CO_2$ in the same leaktight chamber under pressure, the pressure being that of the steam feed of the electrolyzer/co-electrolyzer, typically at 30 bar. In the context of the invention, if it is desired to have methane at the outlet that is at a higher pressure, the steam feed pressure, and consequently that in the chamber, is at this higher pressure. In particular, it may be desired to have methane at the outlet at a pressure of 80 bar which corresponds to the pressure encountered in methane gas pipelines: the feed pressure of steam and in the chamber is thus, in this case, equal to 80 bar.

Thus, as illustrated in FIGS. 3 to 5, the inventors have designed a novel reactor 6 for obtaining methane by heterogeneous catalysis integrating both the electrolysis/co-electrolysis reactor 1 with a stack of SOEC electrolysis cells and the solid catalyst required for the catalytic conversion remote from the electrolysis/co-electrolysis reactor 1.

The methanation reactor 6 first comprises an electrolysis/co-electrolysis reactor 1 housed in a leaktight chamber 7 which can be placed under the given pressure at which the feed steam $H_2O$ arrives in the reactor 1. As illustrated in FIGS. 3 to 5, the chamber 7 of the methanation reactor is of generally cylindrical shape of longitudinal axis X and the reactor 1 is centered on this axis X, i.e. the center not shown of each cells C1, C2, etc. constituting the stack of the reactor 1 is on the axis X.

As illustrated in FIGS. 3 to 5, the leaktight chamber 7 comprises a lid 70, a base 71, and a side envelope 72 assembled both with the lid 70 and the base 71. The base 71 and the lid 70 may be assembled on the side envelope 72 via a bolted flange system equipped with a seal.

To cool the chamber 7, a cooling circuit is provided consisting of a tube 73 wound in a uniform coil on the outer wall of the side envelope 72. This cooling circuit 73 may advantageously cool the inner walls 74 delimiting the chamber 7 below the water saturation temperature at the pressure prevailing in the chamber, advantageously below 230° C. at 30 bar. Thus, as explained more precisely below, the unconverted steam may advantageously be condensed on the inner walls 74 and it is thus possible independently to recover the methane produced and the steam by gravity.

Inside the leaktight chamber 7 is placed a porous partition 8 containing a solid catalyst 80 for converting syngas into methane or a mixture of carbon dioxide $CO_2$ and hydrogen into methane. The solid catalyst may advantageously be Ni—$Al_2O_3$ or Ni—$ZrO_2$ or that mentioned in publication [2], namely the bimetallic catalyst Ni—Fe/γ-$Al_2O_3$ which has excellent catalytic properties for methanation at a pressure of 30 bar.

As illustrated in FIGS. 3 to 5, the porous partition 8 consists of two metal walls 81, 82 each formed from a sheet pierced with a plurality of holes 83 regularly spaced both over the height and over the length of the partition 8, the height being the dimension of the partition according to the axis X, the length being its circumference around the axis X. In addition to the uniform distribution of the holes 83, a hole 83 of one of the walls 81 is provided facing a hole 83 of the other of the walls 82. Conversely, an offset may also be provided between these holes 83 from one wall 81 to the other 82.

As also illustrated, the partition 8 is closed on itself forming a cylinder arranged concentrically around and at a distance from the reactor 1. Finally, a lid 84 different from that of the chamber 7 closes the inner volume delimited by the porous partition 8. Thus, the presence of the lid 84 makes it possible to force the gas to pass through the catalyst in order to emerge from the chamber. The space separating the two sheets 81, 82 is filled with conversion catalyst 80. This catalyst is advantageously in the form of powder which may be introduced into the space between the two sheets 81, 82 before closure with the lid 84. Closure of the lid on the sheets may advantageously be performed by welding or by any other mechanical fixing means. The mechanical fixing means do not have to be dimensioned to withstand a substantial force, since this (these) means are not stressed by the pressure prevailing in the chamber 7. It may be, for example, an attachment of cleat type, a screw through the lid 84 entering the wall 82.

As illustrated in FIGS. 3 to 5, a first support 9 is placed in the chamber 7 to support both the electrolysis or co-electrolysis reactor 1 and the porous partition 8 so as to place them at a distance from the base 71 and from the lid 70 of the chamber 7. This first support 9 also closes the volume below the partition 8 and of the reactor 1.

As illustrated in FIGS. 3 to 5, a second support 10 is provided, fixed onto the first support 9, to support only the electrolysis or co-electrolysis reactor 1 so as to place it facing the central portion of the porous partition 8.

Preferably, the reactor 1 is halfway up the porous partition 8, i.e. placed facing a portion located halfway up the height of the walls 81, 82. This makes it possible firstly to have a homogeneous thermal gradient in the inner volume delimited by the wall 81 and secondly to have homogeneous distribution of the gases ($H_2$ and CO or $H_2$ and $CO_2$) leaving the reactor 1 in this inner volume and thus homogeneous distribution of the gases to be converted into methane during their entry into the catalyst 80. Needless to say, as explained in detail below, the thermal gradient between the reactor 1 and the porous partition 8 is necessary due to the difference in reaction temperature between, on the one hand, that for the electrolysis of steam or the co-electrolysis of steam and $CO_2$, advantageously of about 800° C., and, on the other hand, that for methanation, advantageously about 400° C.

Thus, a concentric arrangement of the porous partition 8 containing the conversion catalyst 80 around the reactor 1, a uniform distribution of the holes 83 for passage of the gases ($H_2$ and CO or $H_2$ and $CO_2$) leaving the reactor 1 and an arrangement of the reactor 1 halfway up the partition 8 contribute toward a very homogeneous thermal gradient in the inner volume delimited by the partition 8, its lid 84 and the support 9 and very homogeneous distribution of the gases ($H_2$ and CO or $H_2$ and $CO_2$) in this inner volume. The path of the gases in the catalyst 80 may be relatively short, even for a large amount of catalyst present between the walls 81, 82, which is advantageous for the thermal management of the methanation reaction over the entire circumference of the partition 8. The thickness of the partition 8, i.e. its smallest dimension transversely to the axis X, may thus be relatively small compared to its other dimensions.

As illustrated in FIGS. 3 to 5, the partition 8 comprises, in the solid catalyst 80, a part of the cooling circuit 85 suitable for cooling the catalytic methanation reaction or, in other words, for maintaining a constant temperature, advantageously of 400° C., for said reaction. Specifically, since the methanation reaction is exothermic, the cooling circuit 85 in the catalyst 80 makes it possible to maintain this catalyst at a suitable temperature, preferably close to 400° C. More precisely, the cooling circuit 85 may comprise a tube wound in a regular coil in the space between the inner wall 81 and the outer wall 82, preferably being close to the inner wall 81. The cooling circuit 85 may contain an oil as cooling agent and may be a closed circuit.

As illustrated in FIGS. 3 to 5, a feed tube 11 is provided to feed steam under pressure and, where appropriate, carbon dioxide to the cathodes of the electrolysis or co-electrolysis reactor 1. This tube 11 passes from the outside through the base 71 of the chamber 7 and the first support 9. It is partly wound on itself close to the reactor 1, preferably around the second support 10 to superheat the steam under pressure and, where appropriate, the carbon dioxide before feeding the cathodes, as explained more precisely below.

To form steam under pressure, a heat exchanger 12 is provided, placed outside the chamber 7, and which constitutes a steam production device or steam generator. To do this, liquid water, compressed beforehand to a given pressure, in a tube 13 feeds the steam generator (SG) 12. In the case of co-electrolysis by the reactor 1, carbon dioxide $CO_2$ is introduced via a tube 14 to be mixed in the SG 12 with the steam formed. It may be envisaged to place the steam generator 12 inside the chamber 7, but, for safety reasons associated with the SG (especially the amount of gas present in the case of depressurization), it is preferable to place it outside as shown.

As a source of heat for the SG 12, use may advantageously be made of the closed cooling circuit 85 of the methanation reaction. Thus, as illustrated in FIGS. 3 to 5, the tube 85 in a regular coil inside the partition 8 and closed on itself passes through the base 71 of the chamber and forms the primary circuit, i.e. that conveying the hottest fluid, of the steam generator-exchanger 12. In other words, the cooling circuit 85 of the catalysis reaction in the partition 8 advantageously constitutes the heat circuit for vaporizing the liquid water under pressure in the SG-exchanger 12.

As illustrated in FIGS. 3 to 5, a tube 15 for injecting carbon dioxide into the inner volume between the electrolysis reactor 1 and the porous partition 8 is provided. This makes it possible to perform a methanation via the direct route between the hydrogen produced by the electrolysis of the steam under pressure in the reactor 1 and the $CO_2$ injected via the holes 16 emerging from the tube 15. Thus, in this direct route, the $H_2+CO_2$ mixture passes through the holes 83 of the partition 8 containing the catalyst 80 to be converted into methane. An advantage subsequent to this injection of cold $CO_2$ via the tube 15 is that of allowing management of the thermal gradient necessary between the electrolysis in the reactor 1 and the catalysis in the catalyst 80 in the partition 8.

As illustrated in FIGS. 3 to 5, a tube 17 is provided for recovering methane produced and a tube 18 is provided for recovering by gravity water condensed on the inner walls 74 delimiting the chamber, each tube 17, 18 passing through the base 71 of the chamber 7. So as not to introduce condensed water into the methane recovery tube 17, this tube protrudes from the base 71. In contrast, the end of the tube 18 for recovering the condensed water by gravity does not protrude from the base 71. It may also be envisaged to place the recovery end of the tube 17 on the lid 70 to definitively ensure that said tube 17 does not recover condensates.

It may be advantageously envisaged to reintroduce the condensed water recovered by the tube 18 into the liquid water inlet 13 at the same pressure, of the SG-heat exchanger 12.

As better illustrated in FIGS. 4 and 5, to achieve uniform diffusion of the carbon dioxide $CO_2$ injected into the inner volume delimited by the porous partition 8, the injection tube 15 is wound on itself forming a circle and being pierced with a plurality of holes 16 regularly distributed along the circle.

This same homogeneous distribution may advantageously be achieved in the inner volume delimited by the porous partition 8, for the hydrogen $H_2$ or the syngas $CO+H_2$ produced in the reactor 1. Thus, as better illustrated in FIGS. 4 and 5, a tube 19 for recovering the hydrogen and, where appropriate, the carbon monoxide produced at the cathodes of the reactor 1 is provided. More precisely, this recovery tube 19 is connected to the outlet of the cathode compartments 50 of the reactor 1 and it is wound on itself forming a circle. It is pierced with a plurality of holes 20 regularly distributed along the circle to homogeneously diffuse the hydrogen and, where appropriate, the carbon monoxide in the inner volume delimited by the porous partition 8.

The functioning of the reactor 6 and methanation system that has just been described will now be indicated more precisely, in reference with a nominal operating point. The operating conditions are as follows:

injection of liquid water at 20° C., and compressed to a pressure of 30 bar by the tube 13 into the steam generator 12;

leaktight maintenance at a pressure of 30 bar of the chamber 7 and maintenance at a constant temperature below 230° C. walls 74;

removal of the steam, where appropriate mixed with $CO_2$ injected at 14, from the SG 12 by the tube 11 at 300° C., at the same pressure of 30 bar;

superheating of the steam to 300° C. and 30 bar, where appropriate mixed with $CO_2$ injected at 14, in the part wound on itself of the tube 11 close to the reactor 1 to reach a temperature of 800° C. at the inlet of this reactor;

when the steam removed in the tube 11 does not contain any $CO_2$, then injection of $CO_2$ at room temperature via the tube 15 with holes 16;

maintenance at constant temperature at about 400° C. of the partition 8;

passage of the $H_2+CO+H_2O$ mixture removed by the tube 19 at the outlet of the co-electrolysis reactor 1, and/or with $CO_2$ injected via the tube 15, into the porous partition 8;

methanation reaction at 400° C. in the partition 8;

removal via the holes 83 of the outer wall 82 of the methane $CH_4$ produced and of the water not converted in the HTE and formed by the methanation in the volume delimited between the partition 8 and the chamber 7;

condensation of the water on walls 74 delimiting chamber 7;

recovery of the methane produced at a pressure of 30 bar via the tube 17;

recovery by gravity via the tube 18 of the liquid water condensed and at a pressure of 30 bar;

reinjection of the liquid water recovered at 30 bar into the steam generator 12.

Under non-nominal operating conditions, it may be envisaged to inject $CO_2$ both via the tube 15 (direct route) and via the tube 14 (indirect route).

The rise of the steam under pressure from 300° C. to 800° C. close to the electrolyzer (co-electrolyzer) 1 may take place solely by the exothermic evolution of the reaction in this reactor. A heating system not shown may also be used.

The reactor 6 and methanation system that have just been described are simple to produce with a low investment cost. In particular, all the walls 81, 82 and lid 84 of the partition 8, the constituents 70, 71, 72 of the chamber 7, the supports 9, 10, the tubes 11, 13, 14, 15, 17, 18, 19, 73, 85 may be made using a relatively inexpensive metal, such as stainless steel 316L. Needless to say, care will be taken to select a suitable metal for the parts that need to withstand the high temperatures of the electrolysis/co-electrolysis, typically 800° C. Thus, for at least the parts of the tubes 11, 19 inside which circulate gases at 800° C. and 30 bar, a production with nickel-based alloys may be envisaged.

The reactor 6 and methanation system that have just been described allow a lower production cost than those of the prior art, especially due to the optimized thermal coupling between the two reactions (electrolysis/co-electrolysis and methanation) in the same chamber 7 under pressure and due to the absence of methane compression equipment, the absence of a pressure chamber specific to methanation, the absence of a condenser at 30 bar, all these functions being performed de facto in the chamber 7.

The invention is not limited to the examples that have just been described; it is especially possible to combine together features of the illustrated examples within variants not illustrated.

Thus, whereas in the detailed implementation example, the reactor 6 and system are envisaged for performing methanation, they may just as equally be envisaged for obtaining methanol $CH_3OH$; DME or diesel. Irrespective of the combustible gas that it is sought to obtain, the following preferred parameters may remain identical:

liquid water feed pressure equal to the pressure of the chamber 7, of about 30 bar, electrolysis or co-electrolysis temperature of about 800° C. to produce $H_2+CO$.

On the other hand, depending on the type of combustible (fuel) targeted, the $H_2/CO$ ratio, the choice of the catalyst 80 and the temperature for the catalysis, i.e. in the porous partition 8, are different. For this last parameter, the partition temperature 8 may be about 400° C. for the production of methane $CH_4$, and about 250° C.-300° C. for methanol $CH_3OH$ and DME.

REFERENCES CITED

[1]: Fabien Ocampo et al., "*Methanation of carbon dioxide over nickel-based Ce0.72Zr0.28O2 mixed oxide catalysts prepared by sol-gel method*", Journal of Applied Catalysis A: General 369 (2009) 90-96;

[2]: Dayan Tiang et al., "*Bimetallic Ni—Fe total-methanation catalyst for the production of substitute natural gas under high pressure*", Journal of Fuel 104 (2013) 224-229.

The invention claimed is:

1. A process for obtaining a combustible gas chosen from methane, methanol, dimethyl ether (DME) and diesel by heterogeneous catalysis, comprising the following steps:

a/ a step of high-temperature electrolysis of steam $H_2O$ performed in an electrolysis reactor housed in a leaktight chamber maintained at a given pressure, in which step a/ each cathode of the reactor is fed with steam at the given pressure;

b/ a step of catalytic conversion performed in at least one reaction zone placed at a distance from and radially to the electrolysis reactor in the same chamber under pressure and containing at least one solid conversion catalyst, step b/ being performed using hydrogen $H_2$ produced during the electrolysis step a/ and carbon dioxide $CO_2$ injected into the space between the electrolysis reactor and the radial reaction zone;

c/ a step of recovery of the combustible gas produced and of the steam not converted in step a/ and produced in step b/, in the space between said radial reaction zone and the wall(s) delimiting the chamber.

2. The process as claimed in claim 1, wherein step b/ is performed with the radial reaction zone closed on itself, being arranged concentrically around the electrolysis or co-electrolysis reactor, respectively.

3. The process as claimed in claim 1, wherein step a/ is performed at temperatures of between 600° C. and 1000° C.

4. The process as claimed in claim 1, wherein step a/ is performed at pressures of between 0 and 100 bar.

5. The process as claimed in claim 1, wherein the walls delimiting the chamber are cooled to a temperature below the water saturation temperature at the given pressure of the chamber, such that step c/ consists of a separation of the combustible gas from the condensed water in the chamber, followed by recovery of the separated combustible gas and of the condensed water by gravity on the bottom of the chamber.

6. The process as claimed in claim 1, constituting a methanation process.

7. The process as claimed in claim 1, wherein the given pressure of the chamber and of operation of the electrolysis or co-electrolysis reactor is equal to about 30 bar, the temperature at which step a/ is performed being maintained equal to about 800° C., the temperature in the radial reaction zone is maintained equal to about 400° C., the temperature of the walls delimiting the chamber is maintained below 230° C.

8. A process for obtaining a combustible gas chosen from methane, methanol, dimethyl ether (DME) and diesel by heterogeneous catalysis, comprising the following steps:

a'/ a step of high-temperature co-electrolysis of steam $H_2O$ and carbon dioxide $CO_2$ performed in a co-electrolysis reactor housed in a leaktight chamber maintained at a given pressure; in which step a'/ each cathode of the reactor is fed with steam $H_2O$ and carbon dioxide $CO_2$ at the given pressure;

b'/ a step of catalytic conversion being performed in at least one reaction zone placed at a distance from and radially to the co-electrolysis reactor in the same chamber under pressure and containing at least one solid conversion catalyst, step b'/ being performed using hydrogen $H_2$ and carbon monoxide CO produced during the co-electrolysis step a'/;

c'/ a step of recovering the combustible gas produced and the steam not converted in step a'/ and produced in step b'/, in the space between said radial reaction zone and the wall(s) delimiting the chamber.

9. The process as claimed in claim 8, wherein step b'/ is performed with the radial reaction zone closed on itself, being arranged concentrically around the electrolysis or co-electrolysis reactor, respectively.

10. The process as claimed in claim 8, wherein step a'/ is performed at temperatures of between 600° C. and 1000° C.

11. The process as claimed in claim 8, wherein step a'/ is performed at pressures of between 0 and 100 bar.

12. The process as claimed in claim 8, wherein the walls delimiting the chamber are cooled to a temperature below the water saturation temperature at the given pressure of the chamber, such that c'/ consists of a separation of the combustible gas from the condensed water in the chamber, followed by recovery of the separated combustible gas and of the condensed water by gravity on the bottom of the chamber.

13. The process as claimed in claim 8, constituting a methanation process.

14. The process as claimed in claim 8, wherein the given pressure of the chamber and of operation of the electrolysis or co-electrolysis reactor is equal to about 30 bar, the temperature at which step a'/ is performed being maintained equal to about 800° C., the temperature in the radial reaction zone is maintained equal to about 400° C., the temperature of the walls delimiting the chamber is maintained below 230° C.

15. A reactor for obtaining a combustible gas chosen from methane, methanol and dimethyl ether (DME) by heterogeneous catalysis, comprising:
a leaktight chamber capable of being placed under a given pressure;
a reactor either for the high-temperature electrolysis of steam or for the high-temperature co-electrolysis of steam and carbon dioxide, comprising a stack of elemental electrolysis cells of SOEC type each formed from a cathode, an anode and an electrolyte intercalated between the cathode and the anode, and a plurality of electrical and fluid interconnectors each arranged between two adjacent elemental cells with one of its faces in electrical contact with the anode of one of the two elemental cells and the other of its faces in electrical contact with the cathode of the other of the two elemental cells, the electrolysis or co-electrolysis reactor being housed in the chamber and the outlet of the cathodes emerging inside the chamber;
at least one porous partition placed at a distance from and radially to the electrolysis or co-electrolysis reactor in the chamber and containing at least one solid catalyst for converting syngas ($H_2$+CO or $H_2$+$CO_2$) into combustible gas;
at least one tube for feeding steam under pressure and, where appropriate, carbon dioxide to the cathodes of the electrolysis or co-electrolysis reactor,
where appropriate, at least one tube for injecting carbon dioxide of the space between the electrolysis reactor and the porous partition;
at least one tube for recovering combustible gas and/or steam,
where appropriate, at least one tube for recovering water condensed on the walls delimiting the chamber, each tube passing through a wall delimiting the chamber.

16. The reactor as claimed in claim 15, wherein the porous partition is closed on itself and is placed concentrically around the electrolysis or co-electrolysis reactor.

17. The reactor as claimed in claim 15, wherein the porous partition consists of two porous metal walls, the space separating them being at least partially filled with a conversion catalyst in the form of powder or granulates.

18. The reactor as claimed in claim 17, wherein the two metal walls each consists of a sheet perforated with a plurality of holes regularly spaced both over the height and over the length of the partition.

19. The reactor as claimed in claim 15, wherein the solid conversion catalyst is based on nickel (Ni) supported on a zirconium oxide ($ZrO_2$), or based on nickel (Ni) supported on an aluminum oxide ($Al_2O_3$), or bimetallic based on nickel (Ni) and iron (Fe) supported on an aluminum oxide ($Al_2O_3$), such as Ni—Fe/$\gamma$-$Al_2O_3$, or based on nickel (Ni) supported on mixed oxides of cerium (Ce) and zirconium, such as $Ce_{0.72}Zr_{0.28}O_2$.

20. The reactor as claimed in claim 15, wherein the porous partition comprises, in the solid catalyst, part of the cooling circuit suitable for cooling the catalytic reaction between the hydrogen and the carbon monoxide produced upstream in the co-electrolysis reactor or between the hydrogen produced upstream in the electrolysis reactor and carbon dioxide injected into the space between the porous partition and the electrolysis reactor.

21. The reactor as claimed in claim 15, wherein the feed tube is partly wound on itself close to the electrolysis or co-electrolysis reactor to heat the steam under pressure and, where appropriate, the carbon dioxide before feeding the cathodes.

22. The reactor as claimed in claim 15, comprising a tube for recovering the hydrogen and, where appropriate, the carbon monoxide produced at the cathodes, the recovery tube being wound on itself forming a circle and being pierced with a plurality of holes regularly distributed along the circle to homogeneously diffuse hydrogen and, where appropriate, carbon monoxide in the space between the electrolysis or co-electrolysis reactor and the porous partition arranged concentrically.

23. The reactor as claimed in claim 15, wherein the carbon dioxide injection tube is wound on itself forming a circle and is pierced with a plurality of holes regularly distributed along the circle to homogeneously diffuse carbon dioxide in the space between the electrolysis or co-electrolysis reactor and the porous partition arranged concentrically.

24. The reactor as claimed in claim 15, wherein the leaktight chamber comprises a side envelope, a lid and a base assembled with the envelope in a leaktight manner, and a first support for supporting both the electrolysis or co-electrolysis reactor and the porous partition so as to arrange them at a distance from the base and from the lid of the chamber.

25. The reactor as claimed in claim 24, comprising a second support, fixed onto the first support, to support only the electrolysis or co-electrolysis reactor so as to arrange it facing the central portion of the porous partition.

26. The reactor as claimed in claim 24, wherein the side envelope comprises a part of a circuit for cooling to a temperature below the water saturation temperature at the given pressure.

27. The reactor as claimed in claim 24, wherein the base constitutes a basin for recovering the water condensed on the lid and/or the side envelope and/or the base.

28. The reactor as claimed in claim 15, being a catalytic reforming reactor and fuel cell, the chamber not being under pressure, the combustible gas recovery tube constituting a combustible gas feed tube and the cell-stack electrolysis or co-electrolysis reactor constituting an SOFC fuel cell.

29. A system comprising:
a reactor as claimed in claim 15;
a heat exchanger forming a steam generator for vaporizing liquid water at the given pressure, the exchanger being placed outside the chamber.

30. The system as claimed in claim 29, wherein part of the secondary circuit of the exchanger comprises the tube for recovering the condensed water in the base.

31. The system as claimed in claim 29, wherein for obtaining a combustible gas, the circuit for cooling the porous partition constitutes the primary circuit of the heat exchanger for vaporizing the liquid water at the given pressure.

32. A process for operating a co-electrolysis reactor in accordance with claim 15, wherein steam is fed and distributed to the cathode of one of the two adjacent elemental cells and carbon dioxide is fed and distributed to the cathode of the other of the two elemental cells.

33. The operating process as claimed in claim 32, wherein an operating regime in exothermic mode is defined for the electrolysis of steam at the cathode of one of the two adjacent elemental cells and an operating regime in endothermic mode is simultaneously performed for the electrolysis of carbon dioxide at the cathode of the other of the two adjacent elemental cells, the heat evolved by the electrolysis of steam being capable of at least partly providing the heat required for the electrolysis of the carbon dioxide.

34. The operating process as claimed in claim 32, wherein an operating regime in exothermic mode is defined for the electrolysis of carbon dioxide at the cathode of one of the two adjacent elemental cells and an operating regime in endothermic mode is simultaneously performed for the electrolysis of steam at the other of the two adjacent elemental cells, the heat evolved by the electrolysis of the carbon dioxide being capable of at least partly providing the heat required for the electrolysis of the steam.

\* \* \* \* \*